(12) United States Patent
Lemper

(10) Patent No.: US 8,967,141 B2
(45) Date of Patent: Mar. 3, 2015

(54) INHALATION SYSTEMS, BREATHING APPARATUSES, AND METHODS

(76) Inventor: Brian Anthony Lemper, Las Vegas, NV (US)

(*) Notice: Subject to any disclaimer, the term of this patent is extended or adjusted under 35 U.S.C. 154(b) by 115 days.

(21) Appl. No.: 13/567,971

(22) Filed: Aug. 6, 2012

(65) Prior Publication Data

US 2013/0061849 A1 Mar. 14, 2013

Related U.S. Application Data

(60) Provisional application No. 61/534,848, filed on Sep. 14, 2011.

(51) Int. Cl.
| | |
|---|---|
| A61M 16/14 | (2006.01) |
| A61M 16/08 | (2006.01) |
| A61K 35/14 | (2006.01) |
| A61M 16/06 | (2006.01) |
| A61M 15/00 | (2006.01) |
| A61M 16/00 | (2006.01) |
| A61M 16/10 | (2006.01) |
| A61M 11/00 | (2006.01) |
| A61M 11/06 | (2006.01) |
| A61M 16/20 | (2006.01) |

(52) U.S. Cl.
CPC ............... *A61K 35/14* (2013.01); *A61M 16/06* (2013.01); *A61M 16/14* (2013.01); *A61M 15/00* (2013.01); *A61M 16/0093* (2014.02); *A61M 16/1065* (2014.02); *A61M 11/005* (2013.01); *A61M 11/06* (2013.01); *A61M 16/0045* (2013.01); *A61M 16/1055* (2013.01); *A61M 16/208* (2013.01); *A61M 2202/0208* (2013.01); *A61M 2202/0415* (2013.01)
USPC ............. 128/203.28; 128/203.12; 128/205.17

(58) Field of Classification Search
USPC ............. 128/200.11–200.23, 203.12–204.14, 128/204.18, 205.17
See application file for complete search history.

(56) References Cited

U.S. PATENT DOCUMENTS

| | | | | |
|---|---|---|---|---|
| 3,809,080 | A | * | 5/1974 | Deaton .................... 128/200.18 |
| 4,703,753 | A | * | 11/1987 | Bordoni et al. .......... 128/200.14 |
| 4,823,784 | A | * | 4/1989 | Bordoni et al. .......... 128/200.14 |
| 5,044,361 | A | | 9/1991 | Werner et al. |
| 5,429,126 | A | * | 7/1995 | Bracken .................... 128/207.11 |

(Continued)

FOREIGN PATENT DOCUMENTS

WO 03/041774 A1 5/2003

OTHER PUBLICATIONS

Roussy, et al., "Activation of human platelet-rich plasmas: effect on growth factors release, cell division and in vivo bone formation", Clinical Oral Implants Research, vol. 18, Issue 5, Oct. 2007, pp. 639-648.

(Continued)

*Primary Examiner* — Valerie L. Skorupa
(74) *Attorney, Agent, or Firm* — Dorsey & Whitney LLP

(57) ABSTRACT

Examples of the invention include inhalation systems, breathing apparatuses, and methods for administering a solution by inhalation to a patient. Example breathing apparatuses described herein may be configured to minimize loss of the solution to the environment. Additionally or instead, example breathing apparatuses may be configured to recirculate exhaled solution to increase an amount of the solution available to a patient while minimizing exhausted solution. In some examples, breathing apparatuses may deliver nebulized platelet rich plasma ("PRP").

12 Claims, 8 Drawing Sheets

(56) References Cited

U.S. PATENT DOCUMENTS

Figure 1:
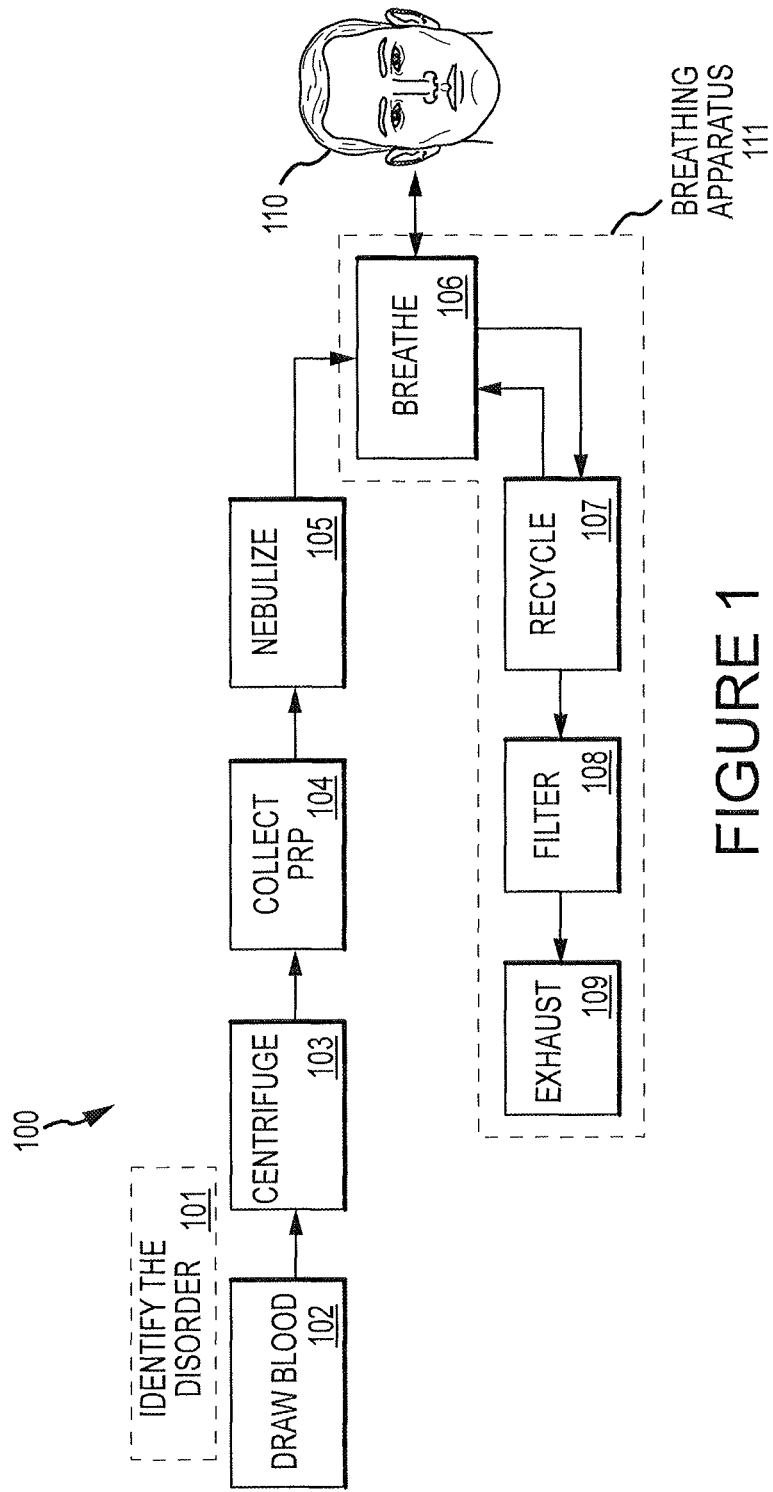

| | | | |
|---|---|---|---|
| 5,603,314 A | 2/1997 | Bono | |
| 5,752,502 A * | 5/1998 | King | 128/200.18 |
| 5,803,078 A * | 9/1998 | Brauner | 128/207.14 |
| 7,191,776 B2 * | 3/2007 | Niles et al. | 128/200.14 |
| 7,418,962 B1 * | 9/2008 | Rao | 128/200.24 |
| 7,819,117 B2 * | 10/2010 | Park | 128/202.26 |
| 2004/0003808 A1 * | 1/2004 | Fuhrman et al. | 128/200.24 |
| 2005/0217667 A1 * | 10/2005 | Dhuper et al. | 128/200.23 |
| 2005/0247310 A1 * | 11/2005 | Grove et al. | 128/201.22 |
| 2007/0102280 A1 * | 5/2007 | Hunter et al. | 204/157.15 |
| 2007/0283951 A1 * | 12/2007 | Burk et al. | 128/200.21 |
| 2010/0112081 A1 * | 5/2010 | Mishra et al. | 424/530 |
| 2011/0005517 A1 * | 1/2011 | Boeck et al. | 128/200.23 |
| 2011/0011395 A1 * | 1/2011 | Mazela et al. | 128/202.13 |
| 2011/0108025 A1 | 5/2011 | Fink et al. | |
| 2012/0087988 A1 * | 4/2012 | Gold | 424/530 |
| 2013/0273008 A1 | 10/2013 | Lemper et al. | |

OTHER PUBLICATIONS

International Search Report and Written Opinion dated Jan. 30, 2013 for Application No. PCT/US2012/049778.

Defendants' Answer to Plaintiffs' Second Amended Complaint and First Amended Counter Claim for Case No. A-12-660850-C, Dept. No. XII, electronically filed on Nov. 25, 2013, pp. 1-27.

* cited by examiner

```
┌─────────────────────────────────────┐
│ DRAW PERIPHERAL VENOUS BLOOD FROM   │──── 601
│         THE PATIENT                 │
└─────────────────────────────────────┘
                 │
                 ▼
┌─────────────────────────────────────┐
│ CENTRIFUGE DRAWN BLOOD TO SEPARATE  │──── 602
│     PLATELET RICH PLASMA (PRP)      │
└─────────────────────────────────────┘
                 │
                 ▼
┌─────────────────────────────────────┐
│    PREPARE PRP COMPOSITION FOR      │──── 603
│    ADMINISTERING TO THE PATIENT     │
└─────────────────────────────────────┘
                 │
                 ▼
┌─────────────────────────────────────┐
│  INJECT THE PRP COMPOSITION IN THE  │──── 604
│         INHALATION DEVICE           │
└─────────────────────────────────────┘
                 │
                 ▼
┌─────────────────────────────────────┐
│      NEBULIZE THE PRP COMPOSITION   │──── 605
└─────────────────────────────────────┘
                 │
                 ▼
┌─────────────────────────────────────┐
│ DELIVER THE NEBULIZED PRP COMPOSITION│──── 606
│      TO THE PATIENT AS A MIST       │
└─────────────────────────────────────┘
                 │
                 ▼
┌─────────────────────────────────────┐
│   RECYCLE CAPTURED UNUSED/ EXHALED  │──── 607
│          PRP COMPOSITION            │
└─────────────────────────────────────┘
                 │
                 ▼
┌─────────────────────────────────────┐
│     FILTER UNUSED PRP COMPOSITION   │──── 608
└─────────────────────────────────────┘
                 │
                 ▼
┌─────────────────────────────────────┐
│  STERILIZED FILTERED PRP COMPOSITION│
│          BEFORE EXHAUST             │──── 609
└─────────────────────────────────────┘
```

FIGURE 7

INHALATION SYSTEMS, BREATHING APPARATUSES, AND METHODS

CROSS-REFERENCE TO RELATED APPLICATION(S)

This application claims the benefit under 35 U.S.C. §119 of the filing date of U.S. Provisional Application 61/534,848, filed Sep. 14, 2011, entitled "Platelet rich plasma/stem cell dispensing system and methods thereof," which application is hereby incorporated by reference in its entirety for any purpose.

TECHNICAL FIELD

Examples described herein relate to inhalation systems, including inhalation systems which may recirculate expired solution. Some examples include systems for delivery of platelet rich plasma for inhalation.

BACKGROUND

Respiratory disorders include diseases that affect the air passages, which may include the nasal passages, the bronchi, and/or lungs. These diseases may range from acute infections, such as pneumonia and bronchitis, to chronic conditions such as asthma and chronic obstructive pulmonary disease. According the World Health Organization, 235 million people worldwide currently suffer from asthma. More than 3 million people worldwide died of Chronic Obstructive Pulmonary Disorder (COPD) in 2005. Further, chronic lower respiratory diseases are the third leading cause of death in the United States while nearly one of every five deaths each year in the United States is caused due to adverse health effects from cigarette smoking, according to the Center for Disease Control and Prevention.

Currently, some of the common treatments employed for respiratory disorders include bronchodilators to open the airways, and steroids and other anti-inflammatory medications to reduce lung inflammation. These treatments only manage symptoms of the disorders, and do not offer a cure. Both bronchodilators and steroids may have undesirable side effects. Particularly, bronchodilators have been known to cause anxiety, muscle tremor, nervousness and palpitations. Further, the United States Food and Drug Administration has reported that some of the bronchodilators may make breathing more difficult. Similarly, corticosteroids may cause systemic side effects such as impaired growth in children, decreased bone mineral density, skin thinning and bruising and cataracts, as well as respiratory infection, weight gain and pharyngitis. Further, corticosteroids only work in about 10% of patients with COPD and are mostly prescribed for asthma management.

Commercially available inhalers may suffer from drawbacks ranging from inaccuracy of dose administered and use of propellants to loss of administered drug to the atmosphere. Further, currently available inhalers are only used for disease management and not treatment or cure of a respiratory disorder.

BRIEF DESCRIPTION OF THE DRAWINGS

FIG. 1 is a block diagram illustrating functions of an inhalation system for delivery of solutions by inhalation with a breathing apparatus in accordance with an embodiment of the present invention.

FIG. 2A is a schematic illustration of an example of a breathing apparatus used for delivery of solutions in accordance with an embodiment of the present invention.

FIG. 2B is a schematic illustration of a filter cap in accordance with an embodiment of the present invention.

FIG. 3 is a schematic illustration of another example of a breathing apparatus including a head strap in accordance with an embodiment of the present invention.

FIG. 4 is a schematic illustration of another example of a breathing apparatus including a nebulizer in accordance with an embodiment of the present invention.

FIG. 5 is a schematic illustration of another example of a breathing apparatus including a PEEP valve in accordance with an embodiment of the present invention.

FIG. 6 is a schematic illustration of a handheld inhalation system according to an embodiment of the present invention.

FIG. 7 is a flowchart of an example method of treatment using a breathing apparatus in accordance with an embodiment of the present invention.

DETAILED DESCRIPTION

Examples of the invention include inhalation systems, breathing apparatuses, and methods for administering a solution by inhalation to a patient. Example breathing apparatuses described herein may be configured to minimize loss of the solution to the environment. Additionally or instead, example breathing apparatuses may be configured to recirculate exhaled solution to increase an amount of the solution available to a patient while minimizing exhausted solution. In some examples, breathing apparatuses may deliver nebulized platelet rich plasma ("PRP"), however other solutions may also be delivered using apparatuses and systems described herein. In some examples, patients may suffer from a respiratory condition which may be treated by delivery of nebulized platelet rich plasma, however patients need not have any particular condition to utilize systems or apparatuses described herein.

Platelet rich plasma (PRP) or platelet rich plasma/stem cell mixture generally refers to blood plasma that has been enriched with platelets. PRP accordingly may contain a variety of growth factors and other cytokines may stimulate healing of bone and tissue. Generally, platelet rich plasma may be obtained from whole blood by mixing the whole blood with an anticoagulant and centrifuging to separate platelet rich plasma from red blood cells and platelet poor plasma.

Activated platelet rich plasma may increase growth factors in human tissues to stimulate revascularization as well as improve alveolar membrane surface integrity, which may facilitate oxygen extraction and gaseous exchange of carbon dioxide (e.g. diminishing pulmonary dead space, decreasing the body's cardiorespiratory work load to maintain an acid base balance). Studies have shown platelet-rich plasma to increase vascular endothelial growth factor (VEGF) as well as platelet derived growth factor (PDSF-BB), transforming growth factor beta (TSF-beta) and have showed delayed release of Inerleukin-1 beta (IL-1-beta). See, for example Y. Roussey, et. al., "Activation of human platelet-rich plasmas: effect on growth factors release, cell division and in vivo bone formation," Clinical Oral Implants Research, Vol. 18, Issue 5, pp. 639-648, October 2007, which article is hereby incorporated by reference in its entirety for any purpose.

Certain details are set forth below to provide a sufficient understanding of examples of the invention. However, it will be clear to one skilled in the art that examples of the invention may be practiced without various of these particular details. In some instances, well-known sample preparation protocols, medical device components, and treatment methods have not been shown in detail in order to avoid unnecessarily obscuring the described embodiments of the invention.

FIG. 1 is a block diagram illustrating functions of an inhalation system for delivery of solutions by inhalation with a breathing apparatus in accordance with an embodiment of the present invention. The inhalation system 100 of FIG. 1 is shown for use in delivering PRP for inhalation. As discussed above, however, in other examples other solutions may be delivered using examples of systems and apparatuses described herein. Solutions which may be delivered using examples of the present invention include, but are not limited to, platelet-rich plasma solutions, including platelet-rich plasma/stem cell solutions (e.g liquids), platelet-poor plasma solutions, whole blood, and synthetic and organic pharmaceutical and/or chemotherapeutic mixtures or compound solutions. Generally, embodiments of breathing apparatuses described herein may be particularly advantageous for delivery of solutions for which loss to the environment is not desirable, either for health reasons (e.g. platelet-rich plasma solutions), or due to the cost of the solution, for example. However, embodiments of the invention are not limited to such solutions, and may generally be used for any solution which it may be desired to deliver to a patient by inhalation.

Referring again to FIG. 1, treatment of a patient may begin at block 101 with identification of a disorder. Identification of a disorder is not necessary to utilize examples of the invention, including the system 100 of FIG. 1. however, a disorder may be identified to indicate that treatment is advantageous using the system 100 of FIG. 1. The example system 100 of FIG. 1 illustrates a system for delivery of PRP, which may be used to treat respiratory disorders and/or simply to improve lung function, even in the absence of disorder. In block 102, peripheral venous blood may be drawn from the patient. In other examples, venous or arterial blood may instead or additionally be used. In block 103, the collected peripheral venous blood may be centrifuged to collect PRP in block 104. Accordingly, in some examples, PRP obtained from a patient's own blood may be delivered to a patient for inhalation. In other examples, blocks 102-104 may not occur, and another provided source of PRP may be used which may or may not be obtained from the patient's own blood (e.g. PRP from another, compatible person, such as from a donor or blood bank, may be delivered to a patient). Platelet rich plasma may be aerosolized in block 105 by, for example, providing the platelet rich plasma to a nebulizer. The aerosolization of PRP may allow a patient 110 to inhale PRP in block 106 as a mist using a breathing apparatus 111, which may initiate inflammatory response in the lungs of the patient. As the patient 110 inhales PRP, the exhaled and unused PRP may be recycled back to the patient 110 in block 107. Any further unused and exhaled PRP may be filtered in block 108 before being released in the atmosphere as clean exhaust in block 109.

In some examples, blocks 106-109 may be performed using a breathing apparatus 111, examples of which are described further below. The blocks 101-105 may be performed by components other than the breathing apparatus, although in some examples some functions of the blocks 101-105 may be integrated into the breathing apparatus 111. For example, as will be described further below, a nebulizer may be attached to or integrated with the breathing apparatus 111 for performance of block 105. In some examples, a centrifuge may additionally or instead be attached to or integrated with the breathing apparatus 111 to perform PRP collection shown in block 104.

FIG. 2A is a schematic illustration of an example of a breathing apparatus used for delivery of solutions in accordance with an embodiment of the present invention. The breathing apparatus 200 includes a breathing mask 201 which may be connected to a connector-tube 202. The connector tube 202 includes an inlet port 203 for delivering a mist (e.g. an aerosolized solution) to be administered to a patient. An end of the connector tube 202 distal to the end with the breathing mask 201 attached, may be connected to a rebreathing chamber 204. The rebreathing chamber 204 may prevent or reduce loss of unused and exhaled aerosolized solution by recycling it back to the patient. For example, the connector tube 202 may form a 'T' junction with a source of mist (e.g. aerosolized solution entering an inlet port 203. The 'T' junction may connect to both the mask 201 and the rebreathing chamber 204. When a patient inhales, the patient may receive mist from the inlet port 203, as well as solution contained in the rebreathing chamber 204. When the patient exhales, exhaled solution may be contained in the rebreathing chamber 204 and may be available to the patient on a subsequent inhalation. During exhalation, aerosolized solution may continue to be delivered through the inlet port 203, and may also be contained in the rebreathing chamber 204 and/or the connector tube 202. During a next inhalation, fresh aerosolized solution delivered through the inlet port 203 either during the inhalation and/or during the exhalation phase and stored in the device may be inhaled by the patient together with previously exhaled solution contained in the rebreathing chamber. In this manner, the rebreathing chamber 204 may reduce an amount of unused solution relative to systems where exhaled solution may not be recycled back to the patient.

The rebreathing chamber 204 may be made of substantially any material suitable for containing exhaled air and solution, and may be flexible in some examples, and may expand and contract in some examples during exhalation and inhalation, respectively. The rebreathing chamber 204 may be further connected to an exhaust tube 205, which may be a corrugated exhaust tube, via an opening 207. The exhaust tube 205 may carry exhaled air and unused solution (e.g. PRP solution), which may have also been recycled through the rebreathing chamber 204, to an outlet for discharge. The exhaust tube 205 may include a cleaning unit 206 located at the distal end of the exhaust tube 205. The cleaning unit 206 may clean (e.g. sterilize in some examples) the exhaust (which may, for example, include PRP) before releasing it to the atmosphere. The cleaning unit may include filters, ultraviolet light sources, and other devices suitable for cleaning and/or sterilizing exhaust from the rebreathing chamber 204. Additionally or instead, a filter 210 may be provided as an exhaust from the connector tube 202. In some examples, the filter 210 may not be present, and the connector tube may be solid across the region shown as containing the filter 210.

Referring back to FIG. 2A, as discussed above, the breathing mask 201 may be connected to a connector tube 202. In one example of the invention the connector tube 202 may be T-shaped with different attachments at each end. As show in FIG. 2A, one end of the connector-tube 202 may be connected to the breathing mask 201 while the other two ends are connected to an inlet port 203 and the rebreathing chamber 204, respectively. The inlet port 203 may be used for delivering mist (e.g. aerosolized PRP solution). As illustrated in FIG. 3 and explained further below, a nebulizer may be attached to the connector tube 202 at the inlet port 203 to aerosolize a solution (e.g. PRP solution) to be administered to a patient. In one example of the invention the connector tube 202 may be made of polypropylene; however, any suitable material may be used in its construction. The connector tube 202 may form an airtight seal with all three attachments (breathing mask 201, inlet port 202 with optional attached nebulize, and rebreathing chamber 203) to reduce or prevent loss of mist (e.g. aerosolized solution), thus increasing the inhalation of the mist.

The rebreathing chamber 204 may be attached to the distal end of the connector tube 202, and may recycle exhaled mist (e.g. PRP aerosolized solution). In one example, the rebreathing chamber 204 may be implemented using a collapsible bag made of rubber. The bag may inflate and deflate as a patient inhales and exhales the mist (e.g. aerosolized PRP solution). One advantage of rebreathing chamber 204 in some examples of the invention may be increased utilization of the mist (e.g. aerosolized PRP solution). In some examples, the collapsible bag may have a non-linear structure, which may generate a swirl of exhaled mist in the rebreathing chamber 204. Without being bound by theory, such a swirl may facilitate recycling of the solution back to the patient for inhalation. The patient may accordingly be able to breathe the same mist (e.g. PRP solution) multiple times, which may increase delivery of the solution (e.g. PRP) to the patient's lungs. In this manner, loss of solution through the corrugated tube 205 without being inhaled first by the patient may be reduced. As a result, the rebreathing chamber 204 may aid in improving inhalation therapy even with a small amount of solution (e.g. PRP obtained from a patient).

Figure 2A:
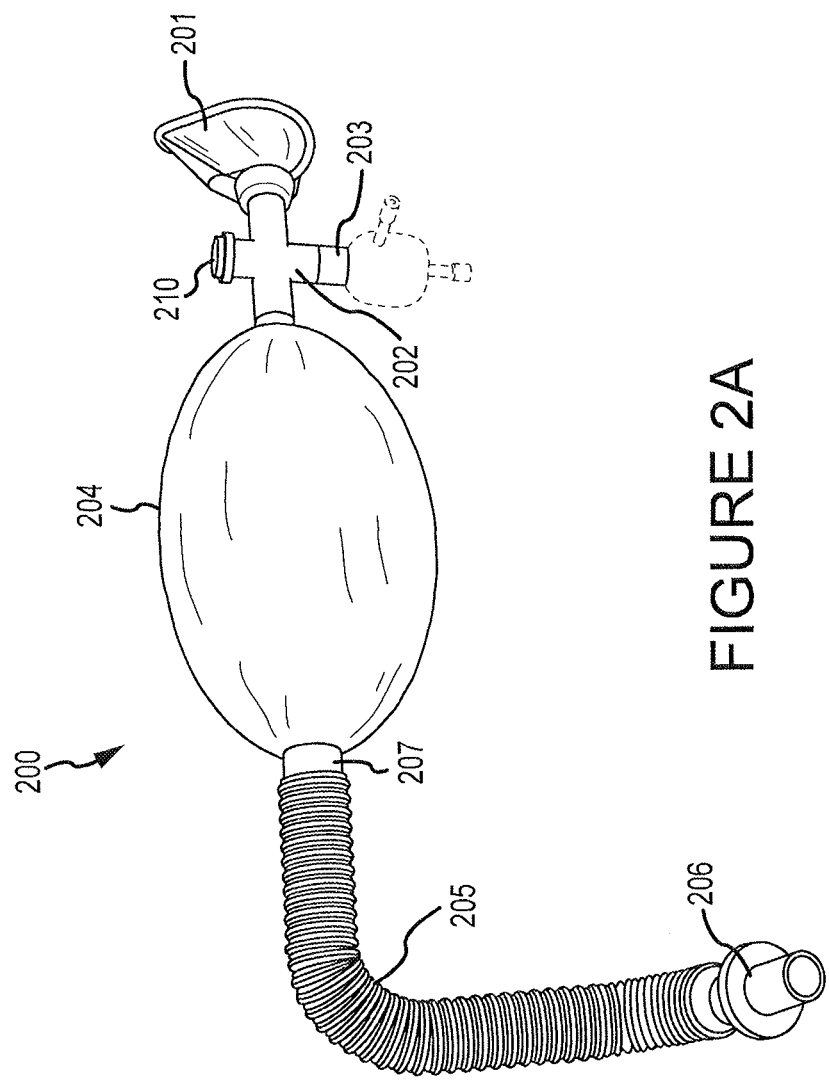
Figure 2B:
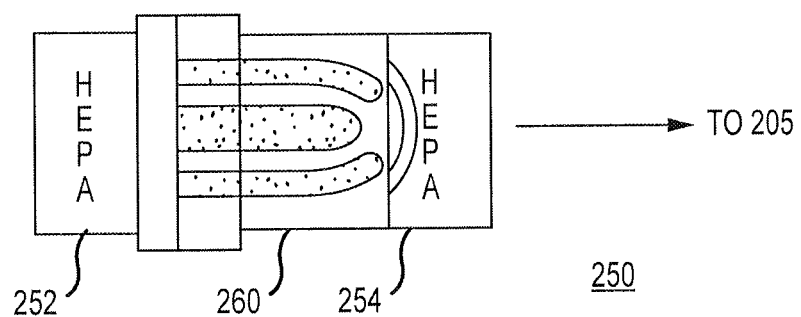

FIG. 2A also shows an exhaust tube 205 connected to the distal end of the rebreathing chamber 204 through an opening 207. The exhaust tube 205, which may be corrugated, may carry ultimately unused/exhaust solution (e.g. PRP) away from the rebreathing chamber and releases it to the atmosphere. The distal end of the corrugated exhaust tube 205 be attached to or integrated into a cleaning system 206 to clean biohazardous material in the exhaust prior to releasing it to the atmosphere. In one example of the invention, the cleaning system 206 may include a High-Efficiency Particulate Filter (HEPA) 408, or a series of HEPA filters. HEPA filters are generally used in various biomedical applications to prevent spread of airborne bacterial and viral organisms. Any suitable type or combination of HEPA filters may be used. In one example, HEPA filter caps may be positioned at the distal end of the tube 205. FIG. 2B is a schematic illustration of a filter cap in accordance with an embodiment of the present invention. The filter cap 250 may be positioned at the distal end of the tube 205 of FIG. 2A. The filter cap 250 may combine two HEPA filters 252, 254 with an activated charcoal mesh 260 with or without silica pillow sandwiched between them. The activated charcoal mesh 260 may increase the effectiveness of a HEPA filter system, while the silicon pillow may absorb any moisture before releasing cleaned exhaust to the atmosphere.

Referring again to FIG. 2A, HEPA filters employed at the distal end of the corrugated exhaust tube 205 and/or at the opening 207 may also create a mild back pressure which may allow for turbulent flow in the rebreathing chamber 204, which may facilitate recycling of the mist (e.g. aerosolized solution) to a patient.

In another example, a high-energy ultra-violet light unit and/or heating coil may be used, additionally to or instead of HEPA filter(s), in the cleaning system 206 to kill any biohazardous material, such as material trapped by the filter media. Of course, it will be apparent to one skilled in the art that various other types of filters and mechanisms may be used alone or in combination in the cleaning system 206.

Figure 3:
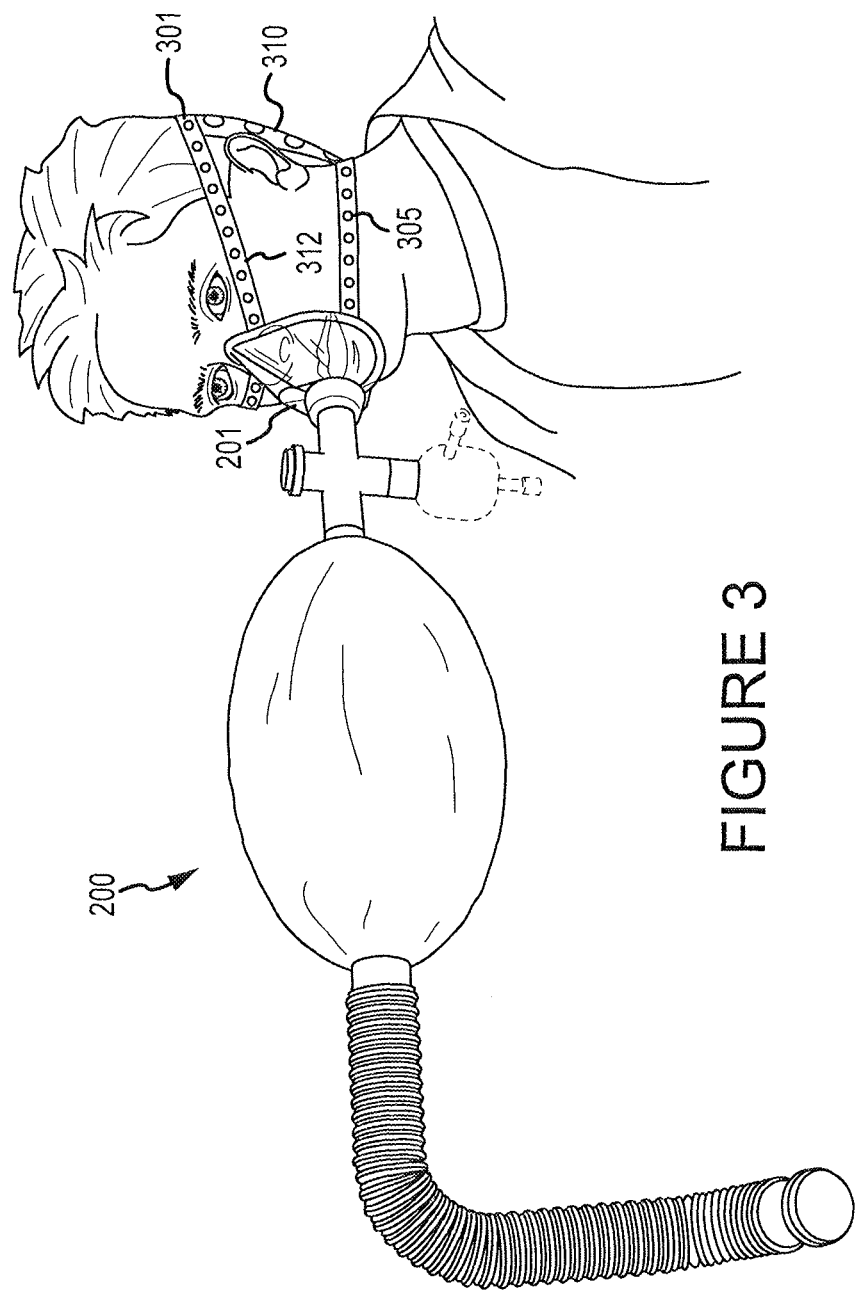

FIG. 3 is a schematic illustration of another example of a breathing apparatus including a head strap in accordance with an embodiment of the present invention. The breathing mask 201 may be fastened to a patient using an anesthesia mask head strap 301. A variety of breathing masks and head strap configurations may be used in different examples of the invention. Generally, breathing masks may be used that advantageously reduce or eliminate the exhaust of mist to the atmosphere. Suitable masks include, but are not limited to, clear plastic oxygen masks, anesthesia masks made of PVC, and soft masks such as those used for sleep apnea treatment. In some examples, the mask may be lined with charcoal to aid in cleaning expired air and/or expired or escaped aerosolized solution. In some examples, one or more filters may be provided in the mask to aid in cleaning expired air and/or expired or escaped aerosolized solution. An anesthesia mask head strap 301 may be used to secure the mask 201 to the patient. Use of an anesthesia mask with a head strap 301 may provide a comfortable fit on a patient's face while preventing loss of any mist (e.g. aerosolized PRP) to the atmosphere. Further, a head strap may allow a patient to conduct other activities, as the patient's hands are not restrained from holding on to the mask, which may increase patient compliance. The head strap 301 shown in FIG. 3 includes a first strap 305 connecting a lower portion of the mask 201 to a support 310 on a back of the patient's head. The head strap 301 includes a second strap 312 connecting an upper portion of the mask 201 to the support 310. Similarly, two straps are present between the mask an the support on the opposite side of the patient's face (not seen in the view of FIG. 3). By providing the support 310 on a back of the patient's head, and a total of four straps from the support 310 to the mask 201, a secure seal may be maintained between the mask 201 and the patient's face. The support 310 and straps 312 may be made of flexible material and may be perforated to allow comfort for the patient's skin in some examples.

Figure 4:
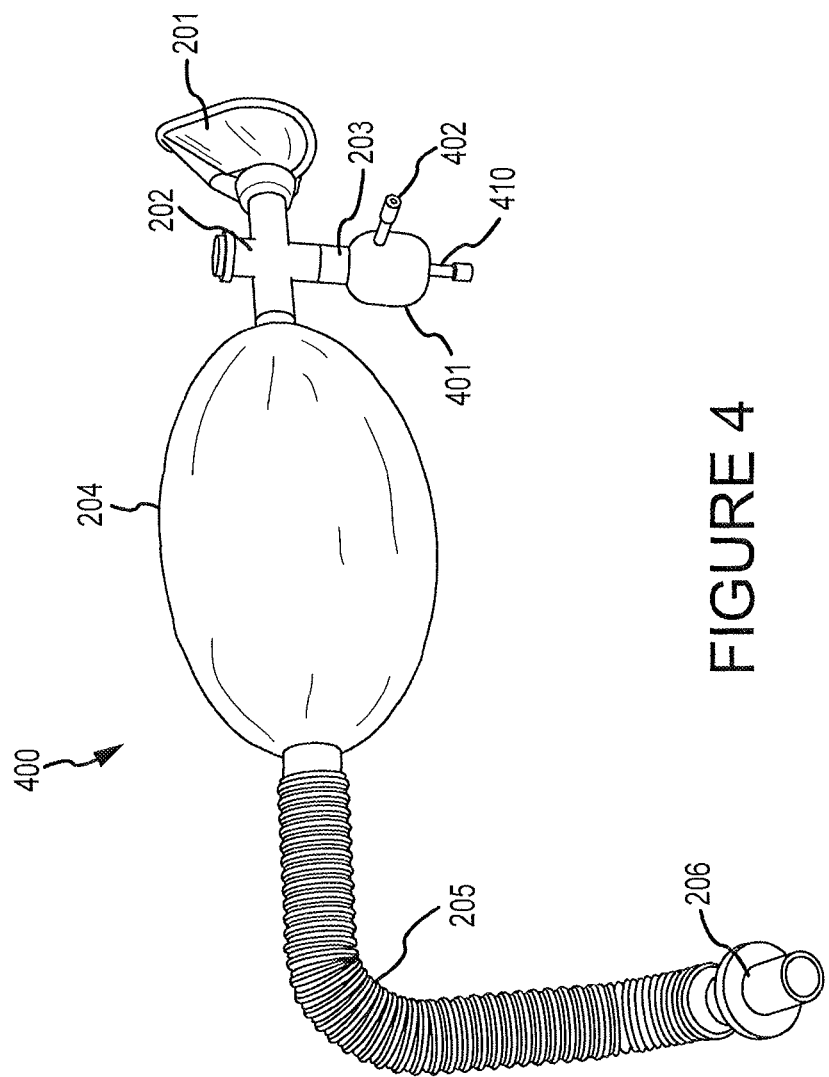

FIG. 4 is a schematic illustration of another example of a breathing apparatus including a nebulizer in accordance with an embodiment of the present invention. Referring to FIG. 4, an example of breathing apparatus 400 with a nebulizer 401 is shown. Like elements of the breathing apparatus 400 are shown with like reference numbers of FIGS. 2-3, and the components will not be described again here for brevity. The breathing apparatus 400 includes a nebulizer 401 attached to or integrated with the breathing apparatus 400 as illustrated in FIG. 4. The nebulizer 401 includes an injection-port 402 for injecting solution (e.g. PRP solution) to be aerosolized. The injection port 402 may be a sterile injection port allowing for the injection of sterile solutions and/or compounds. As is well known in the art, a nebulizer may be used to administer medication in the form of a mist for inhalation in to the lungs. A second port 410, which may be different from the injection port 402, may be provided for gas entry to the nebulizer 401. For example, oxygen may be delivered to the nebulizer 401 to aerosolize a solution contained in the nebulizer 401 and/or introduced to the nebulizer 401 through the injection port 402. Accordingly, in some examples nebulizers may be used having at least two entry ports—one for entry of a gas to facilitate pneumatic nebulizing and another for entry of a solution or compound to be nebulized (e.g. PRP).

The nebulizer 401 is used in an example of the invention to aerosolize a solution (e.g. PRP solution) for administration to a patient. Any suitable nebulizer may be used, including a pneumatic-driven or an ultrasonic nebulizer. The pneumatic-driven nebulizer may require a pressurized gas supply as the driving force for liquid atomization. In one example of the invention, compressed oxygen may be delivered through a plastic tube to the nebulizer 401 (e.g. through the port 410) containing the solution (e.g. PRP solution) which is nebulized in to a mist, and is inhaled by a patient. In another example, an ultrasonic nebulizer may be used where ultrasonic waves are passed through the solution (e.g. PRP solution) to aerosolize it. In the case of ultrasonic nebulizers, the port 410 may not be needed. Aerosolized delivery of PRP may induce inflammation by direct absorption in a patient's lungs. As discussed above, inhalation of aerosolized solution of PRP may allow for treatment of respiratory disorders advantageously without undesirable side effects of steroidal therapies.

In some examples, the nebulizer 401 may be integrated with one or more of the other components shown in FIG. 4. For example, the nebulizer 401 may be integrated with the connector tube 202. In some embodiments of the present invention, a nebulizer may be provided having a port configured to connect to a breathing mask, and a port configured to connect with a rebreathing bag. The nebulizer may have two inlet ports—a sterile inlet port for injection of PRP and another inlet port for entry of a gas for nebulizing, as shown in FIG. 4.

Figure 5:
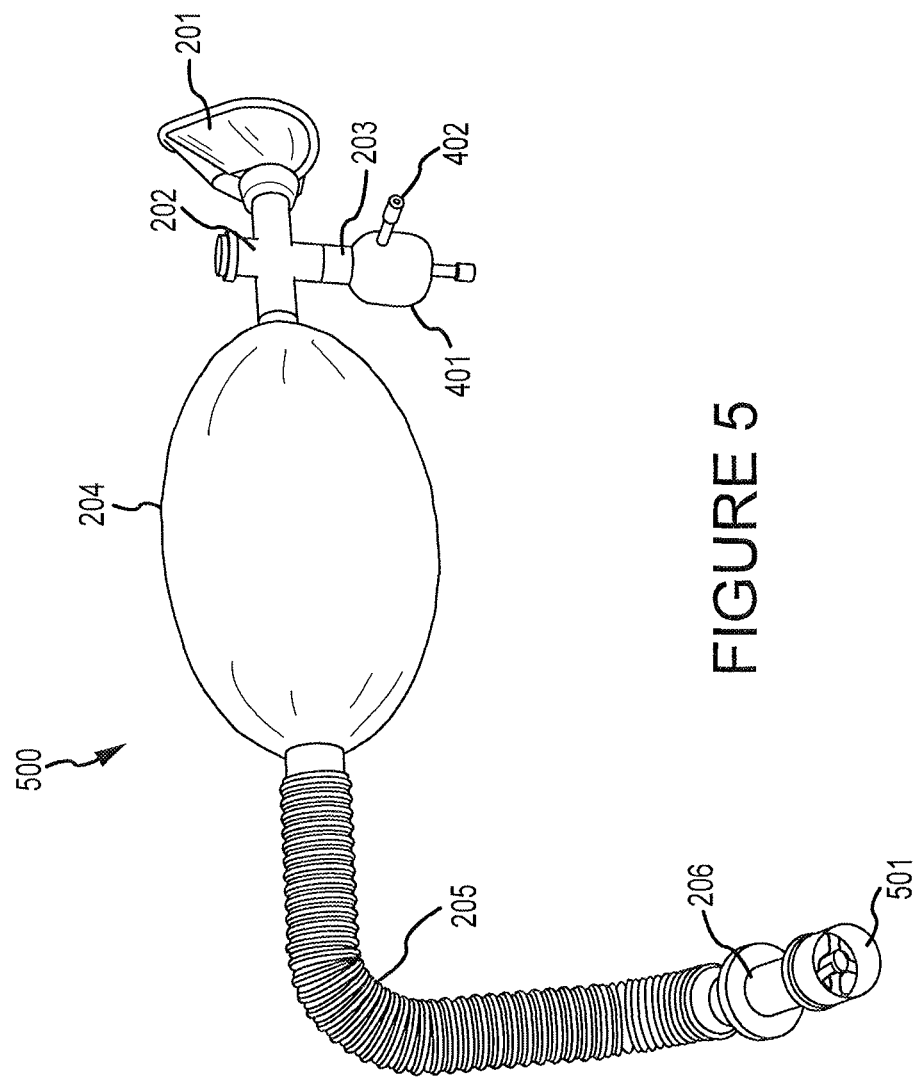

FIG. 5 is a schematic illustration of another example of a breathing apparatus including a PEEP valve in accordance with an embodiment of the present invention. Again, like components are shown with like reference numbers to FIGS. 2-4, and will not be again described here. A heating coil with a fan 501 may be provided at the distal end to implement the cleaning system 206, or to supplement an embodiment of the cleaning system 206. The heating coil may be used to destroy or reduce environmentally hazardous materials as the fan pulls exhaust out. A Positive End-Expiratory Pressure (PEEP) valve may also or instead be used at the distal end of the cleaning system 206, or the distal most end of the breathing apparatus 500. PEEP valves may provide a resistance to exhaled flow, and may advantageously be utilized when the breathing apparatus 500 is used for a patient who is already dependent on ventilation, for example.

Figure 6:
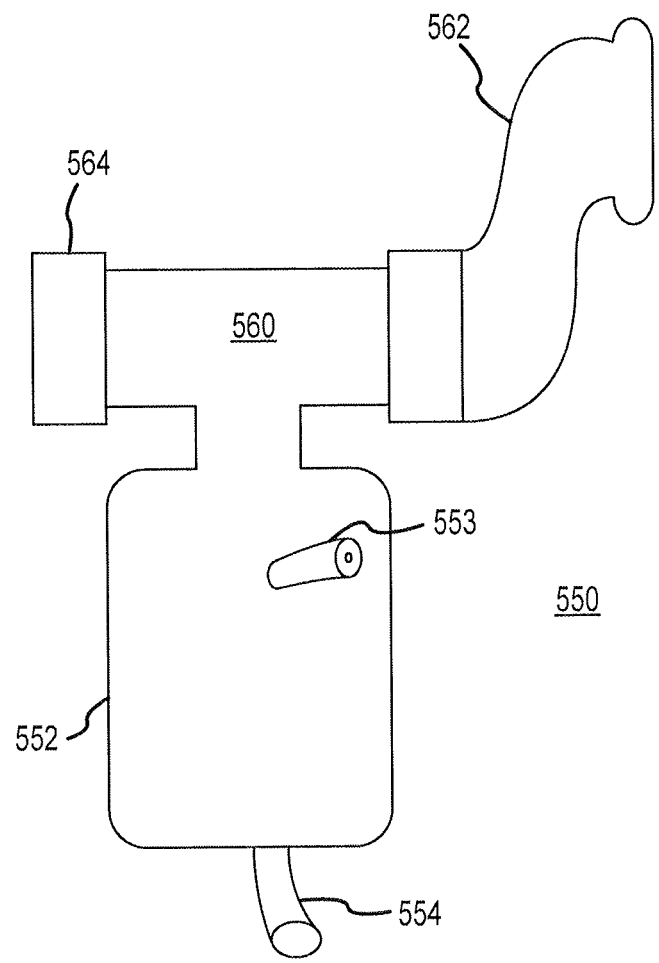

FIG. 6 is a schematic illustration of a handheld inhalation system according to an embodiment of the present invention. Inhalation systems described above with reference to FIGS. 2-5 include examples having a rebreathing chamber for recirculating expired air and/or nebulized solution to a patient. However, examples of the invention include inhalation systems which may not include a rebreathing chamber. For example, the rebreathing chamber 204 may be removed from any of the systems shown in FIGS. 2-4 and, for example, the connector tube 202 of FIG. 2A may be connected to the exhaust tube 205.

Other configurations of inhalation systems are also possible in examples of the present invention. For example, a handheld example is shown in FIG. 6. The handheld inhalation system 550 includes a nebulizer 552. The nebulizer 552 may include a sterile injection port 553 (e.g. for injection of PRP or other solution to be nebulized) and another entry port 554 (e.g. for entry of gas to nebulize the solution or compound in the nebulizer 552. In some examples, the injection port 553 may or may not be present, and PRP or other compound or solution to be nebulized may be provided already in the nebulizer 552. The nebulizer 552 may be connected to a connector tube 560. The connector tube 560 may further be connected to a mouthpiece 562 on one end and a cap 564 on another end. The inhalation system 550 may be sized such that a patient may hold the system 550, e.g. by holding the nebulizer 552, the tube 560, and or the mouthpiece 562.

The cap 564 may include or may be replaced with one or more filters or components of a cleaning system, examples of which have been described above. The mouthpiece 562 may be brought up to a patient's mouth during inhalation, and a patient in some examples may not exhale into the system 550 (such as in some examples when the cap 564 is impermeable to exhaled air and/or solution). In other examples, the patient may exhale into the system 550 through the mouthpiece 562. The mouthpiece 562 in some examples may be replaced with or connected to a face mask, examples of which have been described above.

In still other examples, examples of nebulizers described herein, such as the nebulizer 552 of FIG. 6 or the nebulizer 401 of FIG. 5, may be connected to a tube (e.g. a flexible tube) that may be connected to a ventilator. In this manner, PRP or other nebulized solutions or compounds may be delivered to a patient on a ventilator, including through a tracheotomy tube in some examples.

In some examples, the nebulizer 552 may be integrated with the connector tube 560. Accordingly, in some examples, the nebulizer 552 may have one output port configured to connect to a mouthpiece or a mask and another output port configured to connect to a rebreathing bag and/or an exhalation tube or filter.

FIG. 7 is a flowchart of an example method of treatment using a breathing apparatus in accordance with an embodiment of the present invention. FIG. 7 illustrates an example of the invention including various steps involved in treatment of a respiratory disorder using PRP solution, however as discussed above other disorders may be treated and other solutions delivered in an analogous manner. Once a healthcare provider has identified a respiratory disorder, the treatment may begin with drawing peripheral venous blood from a patient, as in block 601. In other examples, venous or arterial blood may additionally or instead be used. In some examples, a respiratory disorder need not be identified, and a treatment may simply be initiated. Examples of the present invention may advantageously utilize a patient's own blood for treatment with no external medications. In other examples, other blood may be used, and/or external medications may be used additionally or instead.

In one example, a treatment may utilize approximately 60 cc of peripheral venous blood. Approximately 54 cc of drawn blood may be mixed with 6-8 cc of anticoagulant citrate dextrose solution, solution A (ACD-A) and centrifuged at 3200 rpm for 10 minutes with a ramp-up time to 10 minutes continuous spin, in block 602. The amount of blood and centrifugation parameters may vary based on the centrifuging technique used, as is known in the art. PRP may be collected from the centrifuged solution using appropriate techniques, in block 603. PRP may be obtained from a blood sample, from any of the standard existing, or later-developed, commercially available systems.

Generally, PRP may be centrifuged from a blood sample and may appear as a layer between a red blood cell rich portion of the centrifuged blood and the plasma. Approximately 6-9 cc of PRP may be collected (which amount may depend on the harvest yield from centrifugation), with about 16-19 cc of platelet poor plasma (PPP) in one example. For example, the layer of PRP may be collected together with some portion of the adjacent plasma layer and/or a portion of the red blood cell layer. In some examples, the collected PRP, about 6-9 cc, may be diluted with PPP to make an injection volume up to 10 cc in one example. The PRP and any collected platelet poor plasma and/or red blood cells may be mixed in some examples. In block 604, the resulting solution may be injected in the nebulizer 401 through the injection-port 402 for nebulization. In one example of the invention, approximately 10-18 cc of platelet poor plasma may also be injected through the injection-port 402 immediately after injecting the PRP solution. In some examples, PRP and PPP solutions may be administered separately or in various percentages depending on a goal of treatment. In block 605, the injected PRP solution may be nebulized to create aerosolized PRP, which may be inhaled by the patient as a mist in block 606. In examples utilizing a pneumatic nebulizer, a flow of gas may be provided for nebulization. For example, 8-14 liters/minute of oxygen flow may be provided in some examples to nebulize the solution and provide adequate oxygen for inhalations. In some examples, the oxygen may aid in activating the PRP, which may increase therapeutic effect. In some examples, contact between the PRP and plastic portions of the inhalation apparatus used may serve to activate the PRP. Generally, activating PRP refers to initiating the process of PRP producing growth hormones, which may aid in the therapeutic effectiveness of PRP inhalation.

As the patient continues inhaling and exhaling the aerosolized PRP solution any unused and exhaled PRP solution may optionally be captured in the rebreathing chamber 204 in block 607. As described above, in some examples, such as a handheld system example, a rebreathing chamber may not be provided. In some examples, however, in block 607 unused and exhaled aerosolized PRP solution may be recycled back to the patient, thus reducing loss of PRP and increasing the effectiveness and efficiency of the inhalation process in some examples. In block 608, the exhaust tube 205 may carry any residual exhaust to the cleaning system 206 where it may be cleaned by filtration or any other suitable technique before being released to the atmosphere.

The system of administering aerosolized PRP solution and the method of treatment of patients with respiratory disorders using breathing apparatuses described herein, have a wide range of applications in the biomedical world. For example, patients suffering from a respiratory disorder who do not respond to steroidal therapy, want to avoid its undesirable effects, or are not able to afford the therapy because of its prohibitive cost, may benefit from examples of systems, apparatuses, and treatments described herein. As mentioned above, PRP administration by inhalation may include using a patient's own blood for treatment. Examples of the invention have application in a wide range of disease states including chronic obstructive pulmonary disorder, bacterial or viral lung infections (including H5N1, H1N1, and SARS), damage to lungs from smoking, end-stage respiratory disorders, seasonal allergies, sinusitis, pleuritic chest pain, ischemic cardiac pain, and general lung function. Given the flexibility of examples of the invention, embodiments may be used in medical facilities as well as in at-home treatment of patients. Further, the invention is not limited to administering PRP solution, and can be used for delivery by inhalation of any solution while advantageously reducing loss and increasing efficiency of delivery, while minimizing release of chemicals or substances in to the atmosphere.

From the foregoing it will be appreciated that, although specific examples of the invention have been described herein for purposes of illustration, various modifications may be made without deviating from the spirit and scope of the invention, such as but not limited to incorporating various components into a single component for ease of manufacturing or patient ease of handling.

What is claimed is:

1. A system for administering a platelets rich plasma solution to an individual by inhalation, the system comprising:
    a nebulizer including a sterile port for receiving the platelets rich plasma solution;
    a connector tube coupled to the nebulizer and configured to receive a mist of the platelets rich plasma solution through an inlet port of the connector tube;
    a breathing mask connected to the connector tube and configured to deliver the mist to the individual;
    a rebreathing chamber connected to the connector tube and configured to receive an exhaled portion of the mist from the individual and recycle at least some of the exhaled portion back to the individual, the rebreathing chamber comprising;
        a first end connected to the connector tube; and
        a second end opposite the first end;
    an exhaust tube connected at a proximal end of the exhaust tube to the second end of the rebreathing chamber and configured to collect an exhaust portion of the mist; and
    a cleaning unit connected to a distal end of the exhaust tube and configured to clean the exhaust portion of the mist.

2. The system of claim 1, wherein the breathing mask includes a head strap configured to fasten the breathing mask to the individual.

3. The system of claim 2, wherein the head strap is connected to a support configured for positioning at a back of the individual's head.

4. The system of claim 1, wherein the nebulizer is an air-flow driven nebulizer.

5. The system of claim 4 wherein the nebulizer is an ultrasonic nebulizer.

6. The system of claim 1 wherein the cleaning unit comprises a HEPA filter.

7. The system of claim 6, wherein the cleaning unit includes multiple HEPA filters connected in series.

8. The system of claim 6 further comprising another HEPA filter at a distal end of the rebreathing chamber.

9. The system of claim 6, further comprising an ultra violet cleaning unit at a distal end of the HEPA filter.

10. The system of claim 1, further comprising a positive end-expiratory pressure valve at a distal end of the cleaning unit.

11. The system of claim 1, wherein the cleaning unit includes a pair of HEPA filters and a charcoal activated mesh disposed between the HEPA filters.

12. The system of claim 11, wherein the cleaning unit further includes a silicon pillow disposed between the HEPA filters for absorbing moisture from the exhaust tube.

* * * * *